United States Patent
Bottom et al.

(10) Patent No.: US 7,490,607 B2
(45) Date of Patent: Feb. 17, 2009

(54) ANESTHETIC AGENT CASSETTE FOR AN ANESTHESIA MACHINE

(75) Inventors: Douglas K. Bottom, Watertown, WI (US); Clifford G. Kersey, Oregon, WI (US); Steven A. Jandl, Lodi, WI (US); John E. Klaus, Cottage Grove, WI (US)

(73) Assignee: The General Electric Company, Schenectady, NY (US)

( * ) Notice: Subject to any disclaimer, the term of this patent is extended or adjusted under 35 U.S.C. 154(b) by 709 days.

(21) Appl. No.: 11/103,167

(22) Filed: Apr. 11, 2005

(65) Prior Publication Data

US 2006/0225735 A1    Oct. 12, 2006

(51) Int. Cl.
*A61M 11/00*    (2006.01)
(52) U.S. Cl. ............................. 128/203.12; 128/203.15
(58) Field of Classification Search ............ 128/203.12, 128/203.15; 604/20; 424/45
See application file for complete search history.

(56) References Cited

U.S. PATENT DOCUMENTS

| | | | | |
|---|---|---|---|---|
| 4,890,479 | A | * | 1/1990 | Glover et al. ............... 73/23.31 |
| 5,237,990 | A | * | 8/1993 | Psaros et al. ........... 128/204.21 |
| 5,592,934 | A | * | 1/1997 | Thwaites ................ 128/203.12 |
| 6,585,016 | B1 | | 7/2003 | Falligant et al. |
| 6,745,800 | B1 | | 6/2004 | Sansom |

FOREIGN PATENT DOCUMENTS

| | | |
|---|---|---|
| DE | 101 06 010 | 7/2002 |
| GB | 2 254 005 | 9/1992 |

OTHER PUBLICATIONS

S/5™ Anesthesia Delivery Unit Aladin™ Cassette; Datex-Ohmeda Division, Instrumentarium Corp., P.O. Box 900, FIN-00031, Datex-Ohmeda, Finland; www.datex-ohmeda.com, last visited Apr. 11, 2005.

* cited by examiner

*Primary Examiner*—Steven O Douglas
(74) *Attorney, Agent, or Firm*—Andrus, Sceales, Starke & Sawall, LLP

(57) ABSTRACT

A cassette for vaporization of anesthetic agent for delivery to a patient is arranged to be received by an anesthesia machine which has control mechanisms for controlling vaporization of the agent. In a preferred arrangement, the cassette includes a housing for receiving, containing and emitting anesthetic agent. A sensor, such as a pressure sensor or a temperature sensor is embedded in the housing for obtaining a value of the agent contained in the reservoir. The sensor is operatively connected to the reservoir to obtain an accurate value of the agent. A communication link is provided between the sensor and the control mechanisms of the anesthesia machine when the cassette is received by the anesthesia machine. The cassette thus provides a simplified arrangement that efficiently and accurately provides values of the anesthetic agent being vaporized in the reservoir.

18 Claims, 3 Drawing Sheets

ANESTHETIC AGENT CASSETTE FOR AN ANESTHESIA MACHINE

BACKGROUND OF THE INVENTION

The present invention generally relates to an arrangement for controlling vaporization of anesthetic agent for delivery to a patient. More specifically, the present invention relates to a cassette that is arranged to be removably received by an anesthesia machine. The cassette includes a housing having an anesthetic agent reservoir for containing anesthetic agent and at least one sensor embedded in the housing and operatively connected to the reservoir to obtain a value of the agent contained in the reservoir.

During the supply of anesthesia, the gaseous anesthetic agent inhaled by the patient is formed of oxygen, nitrogen, nitrous oxide and an inhalation anesthetic agent. Inhalation anesthetics are typically in liquid form at administration temperatures, and an anesthetic vaporizer is needed to gasify the liquid. Anesthetic vaporizers have a drug reservoir for storing the supply of agent to be vaporized.

It is known to provide such a drug reservoir in the form of a module or cassette, such as the Aladin model available from Datex-Ohmeda, Inc., Madison, Wis. The cassette is removable from the anesthesia machine such that different types of anesthetic agents can be supplied to the anesthesia machine by simply removing the cassette and replacing it with a different cassette for a different anesthetic agent. The cassette includes a drug reservoir that contains the supply of anesthetic agent to be delivered to a patient.

In such known arrangements, there are provided controls in the anesthesia machine for vaporizing anesthetic agent to a desired concentration. Known anesthetic agent controls consist of two parts: the actuator mechanisms in the anesthesia machine and the separate sensing mechanisms in the anesthesia machine. In such known arrangements, a temperature measuring sensor from the anesthesia machine is positioned on the outside of the cassette at the rear of the cassette housing, wherein the approximate temperature of the agent is measured. The approximate pressure inside the cassette is measured from the cassette flow after entering the anesthesia machine. Fresh gas content (oxygen and nitrous oxide/air) is taken into account to help achieve greater accuracy. It is recognized as important to obtain a timely and accurate reading of the temperature of the anesthetic agent contained in the cassette reservoir at any time during cassette operation.

It is further recognized as desirable to eliminate any unnecessary control mechanisms and duplicative components within the cassette/anesthesia machine arrangement. Other known arrangements include duplicative control mechanisms and components placed internal to each removable vaporizer, which complicate the system.

SUMMARY OF THE INVENTION

The present invention provides a novel arrangement for a cassette or module for vaporization of anesthetic agent for delivery to a patient when the cassette or module is received by an anesthesia machine. According to the present invention, a cassette is provided that ensures timely and precise measurement of physical properties of anesthetic agent within the cassette. The unique arrangement described and claimed herein eliminates unnecessary control mechanisms and components from the cassette/anesthesia machine arrangement, and yet provides accurate values for the anesthetic agent in a timely and efficient manner. The cassette is inexpensive to produce and eliminates many potential maintenance difficulties that can be incurred by previous removable vaporizer arrangements.

In a preferred arrangement, the cassette for vaporization of anesthetic agent for delivery to a patient is arranged to be received by an anesthesia machine having mechanisms for controlling vaporization of the anesthetic agent. In such an arrangement, the cassette includes a housing having a reservoir for receiving, containing, and emitting anesthetic agent. A sensor is embedded within the housing and is capable of obtaining a value of the agent contained within the reservoir. The sensor can be, for example, a temperature sensor or a pressure sensor. The sensor is operatively connected to the reservoir to obtain an accurate value of the agent. This is contrary to existing cassettes, which place sensors on the exterior of the housing and are only capable of obtaining indirect, and often inaccurate values of the anesthetic agent. A communication link is provided between the sensor and the control mechanisms of the anesthesia machine when the cassette is received by the anesthesia machine. As such, the anesthesia machine is in direct communication with the cassette and, more specifically is arranged to obtain the accurate values detected by the sensor.

The cassette may comprise a variety of sensors, such as pressure and/or temperature sensors that are arranged in accordance with the present invention. In one arrangement, an absorbent wick is contained within the housing for obtaining anesthetic agent and allowing anesthetic agent to vaporize into gas for delivery to a patient. In such an arrangement, a sensor, such as a temperature sensor, is placed in direct contact with the absorbent wick at a predetermined location that is optimal for obtaining temperature values of the anesthetic agent being vaporized from the surface of the absorbent wick. In such an arrangement, the sensor may be secured against the absorbent wick by a bracket that is also formed of absorbent wick material.

BRIEF DESCRIPTION OF THE DRAWINGS

The best mode of carrying out a preferred embodiment of the present invention is described herein below with reference to the following drawing figures, wherein.

DETAILED DESCRIPTION OF THE PREFERRED EMBODIMENTS

The best mode of a preferred embodiment of the present invention is described herein below with reference to the attached drawing figures. It should be recognized that the arrangement discussed and depicted herein is an example of the principles of the invention, which is more particularly defined in the appended claims. The invention is not limited to the particular arrangement discussed and shown hereinbelow. Alternative and equivalent structures and functions that are not discussed below and that fall within the scope of the appended claims are the subject matter of the present invention.

Figure 1:
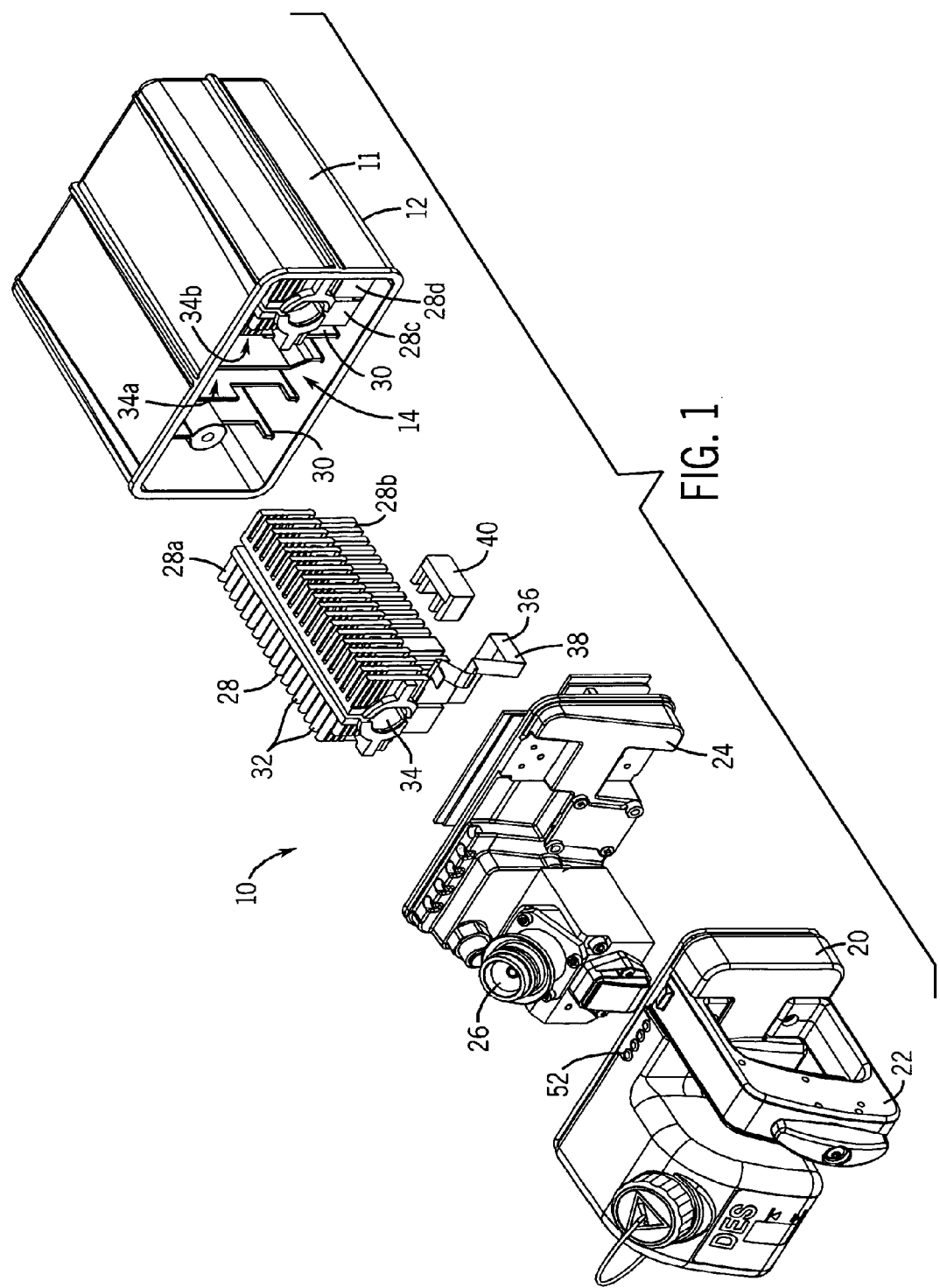
FIG. 1 is an exploded view of a cassette for vaporization of anesthetic agent for delivery to a patient.
Figure 4:
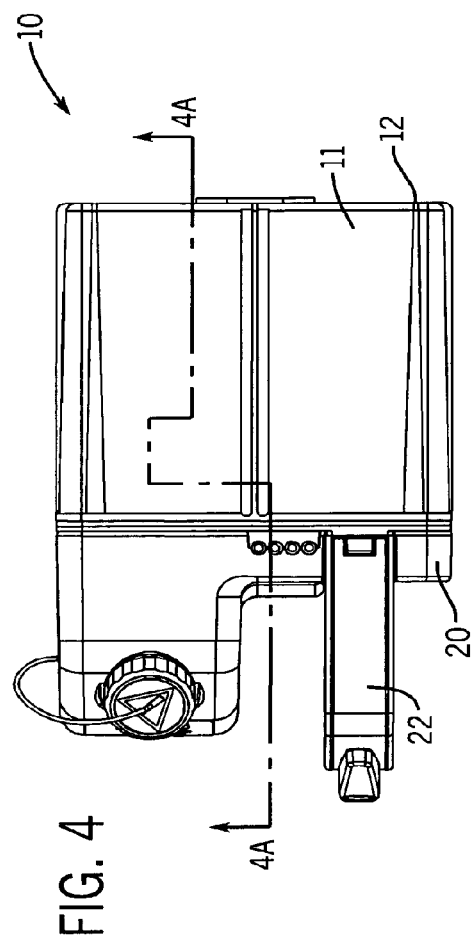
FIG. 4 is a top view of the cassette shown in FIG. 1.
Figure 4A:
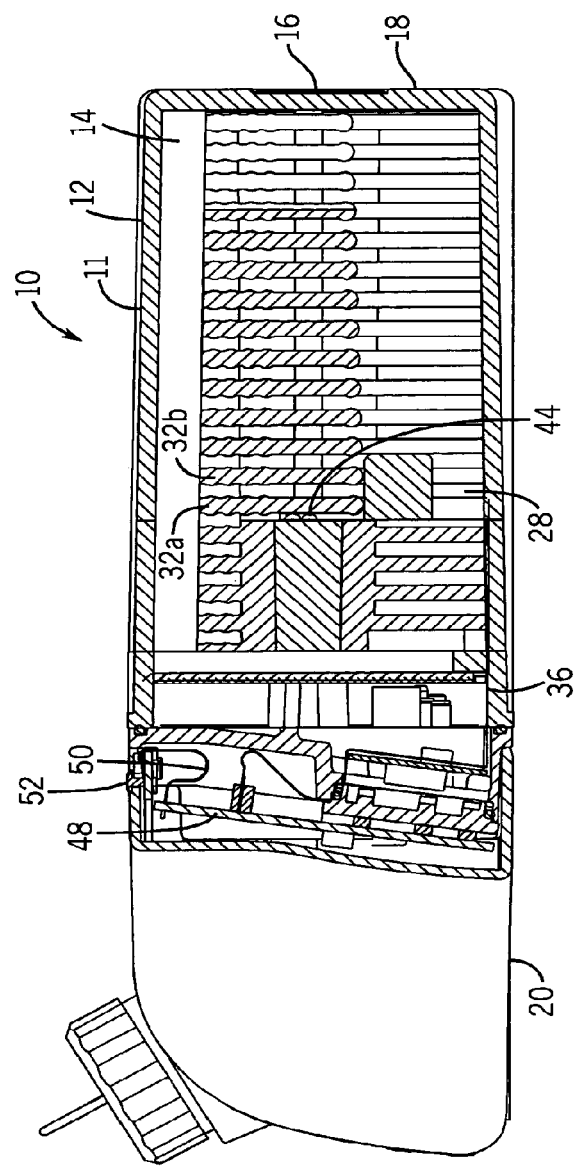
FIG. 4A is a side view of section A-A shown in FIG. 4.

Referring generally to FIGS. 1, 4 and 4A, a module or cassette 10 is shown. The cassette 10 is fashioned after the Aladin cassette model available from Datex-Ohmeda, Inc., Madison, Wis. The cassette 10 is removable from an anesthesia machine (not shown) such that a supply of anesthetic agent can be removed from the cassette 10 and such that different types of anesthetic agents can be supplied to the anesthesia machine by simply removing the cassette 10 and replacing it with a different cassette for a different anesthetic agent. The particular cassette 10 shown is useful with a particular anesthetic agent, namely Desflurane, although it should be recognized that the cassette could be utilized with other types of anesthetic agent while operating within the scope of the present invention.

The cassette 10 includes a housing 11 having a drug reservoir 12 that contains a supply of anesthetic agent to be delivered to a patient. The drug reservoir 12, as depicted in FIGS. 1 and 4A includes an open interior 14 that receives a stored supply of anesthetic agent (not shown). The drug reservoir 12 has a discharge opening 16 formed in the back wall 18 of the housing 11 that can be arranged to receive a discharge tube (not shown) which is part of the anesthesia machine. Typically the reservoir 12 plugs into the anesthesia machine (not shown) such that the discharge tube is received within the discharge opening 16 and forms a gas-tight seal for delivery of anesthetic vapor to a patient.

Figure 3:
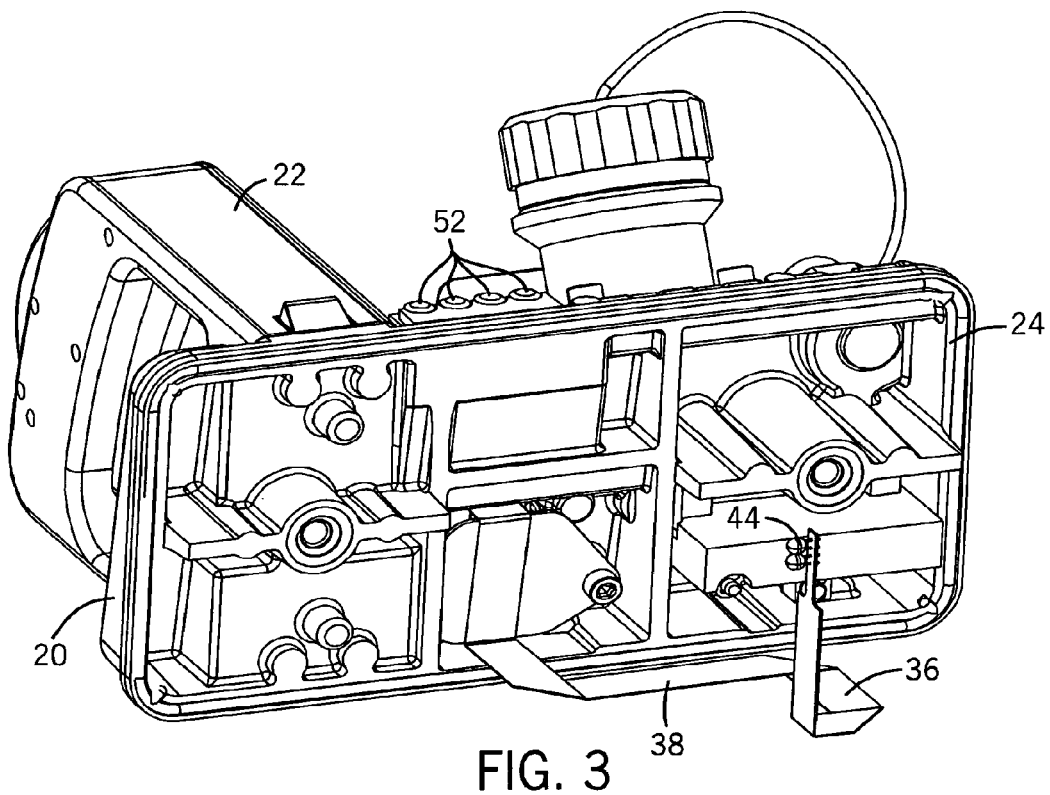
FIG. 3 is a rear perspective view of the front cover of the cassette.

Referring to FIGS. 1 and 3, the cassette 10 also includes a front cover 20 including a handle 22. The front cover encloses a filling device 24 having a filler port 26. When the cassette 10 is assembled, the filler port 26 is sandwiched between the front cover 20 and reservoir 12, as shown in FIG. 4A. As is known in the art, the filler port is arranged to receive a bottle or bottle adapter containing a supply of anesthetic liquid which, in the arrangement shown, would be Desflurane. The interaction between the filler port 26 and the bottle of anesthetic liquid allows only a single type of anesthetic agent to be dispensed into the reservoir 12 of the cassette 10. A different cassette, including a specific filler port 26 is required for dispensing each type of anesthetic agent. In this manner, the improper delivery of an anesthetic agent can be eliminated. Via the filler port 26, the anesthetic liquid flows into the cassette 10 and settles by gravity on the bottom of the reservoir 12.

Figure 2:
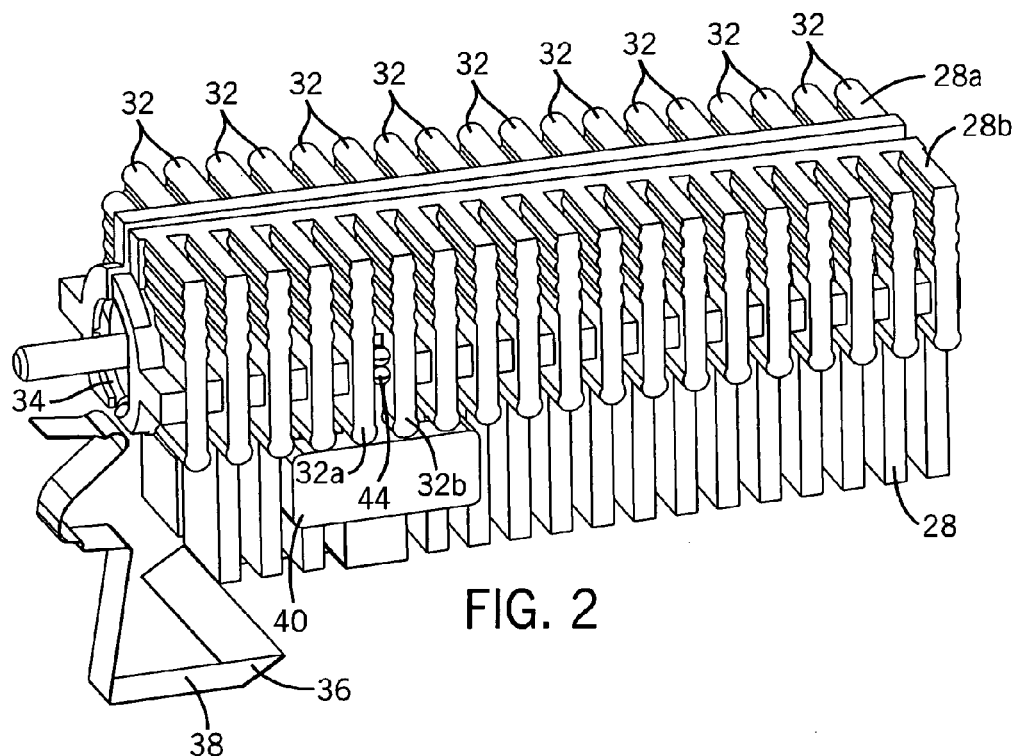
FIG. 2 is a side perspective view of an absorbent wick that is contained within the cassette.

Referring to FIGS. 1, 2 and 4A, at least one absorbent wick 28 is contained within the reservoir 12. In the arrangement shown, two pairs of absorbent wicks 28a, 28b and 28c, 28d are contained within the reservoir 12 and separated by partitions 30. The absorbent wicks 28 are preferably formed from a material that absorbs the particular anesthetic agent contained within the drug reservoir 12. Such absorbent material can be, for example, polyethylene.

Each pair of absorbent wicks 28a, 28b and 28c, 28d comprise a plurality of ribbed surfaces 32 to increase the total surface area from which the anesthetic agent can be vaporized. Passageway 34b allows fresh gas to pass to the first set of absorbent wicks 28c, 28d. Passageway 34a allows the vaporized liquid from absorbent wicks 28a, 28b, 28c, and 28d and accompanying fresh gas to flow to the back 18 of the drug reservoir 12 and out the discharge opening 16 in the housing 11. As is known in the art, a lower portion of the drug reservoir contains the liquid anesthetic agent and an upper portion of the reservoir 12 contains the vaporized anesthetic agent and breathing gases. During operation, a combination of temperature and pressure affect the liquid anesthetic agent and cause it to vaporize into the breathing gases. The gases carrying the vaporized agent are then discharged through the discharge opening 16.

As shown in the figures, the cassette 10 includes an embedded sensor device 36 for obtaining a value of the agent contained in the reservoir 12. Advantageously, the sensor device 36 is operatively connected to the reservoir to obtain an accurate value of the agent. In the arrangement shown, the sensor device includes a flexible circuit board or ribbon of flex circuit 38. With particular reference to FIG. 2, the flex circuit 38 is disposed in the reservoir 12 and in the absorbent wick 28 between ribbed surfaces 32a, 32b. An attachment bracket 40 is provided to secure the flex circuit 38 to the absorbent wick 28 and particularly between the ribbed surfaces 32a, 32b. In a preferred arrangement, the bracket 40 is formed from absorbent wick material, such as polyethylene.

As shown in FIGS. 2 and 4A, the distal end 42 of the flex circuit 38 carries a sensor 44. In the arrangement shown, the sensor 44 is a temperature sensor that senses the temperature of anesthetic agent vapor in the reservoir, such as a thermistor. In the arrangement shown, the sensor 44 is optimally placed within the absorbent wick 28 such that during vaporization of anesthetic agent, the sensor 44 is positioned near the last place where anesthetic agent could evaporate from the ribbed surfaces 32. It will also be appreciated that the sensor 44 could be placed at other positions within the reservoir 12 or at a distance from the wick 28, if desired.

Although the arrangement depicted and described herein provides a sensor device 36 that is arranged to sense the temperature of the anesthetic agent vapor, it will be recognized by those skilled in the art that various other types of sensor devices could be provided and operated within the scope of the present invention. For example, the sensor device 36 may include a pressure sensor that senses the pressure of the fresh gas and anesthetic agent vapor in the reservoir.

Referring to FIG. 4A, the flex circuit 38 provides a communication link between the sensor 44 and the control mechanisms of the anesthesia machine (not shown) when the cassette 10 is received by the anesthesia machine. As shown in FIGS. 2 and 4A, the flex circuit 38 extends from the absorbent wick 28, through the filler device 24 of the cassette 10 and is mounted to a circuit board 48. An electrical connection 50 is provided between the circuit board 48 and a series of electrical contacts 52 on the front cover 20. The electrical contacts 52 are connected to the anesthesia machine when the cassette 10 is inserted therein. As such, a connection is provided between the sensor 44 and the anesthesia machine, allowing the anesthesia machine and control mechanisms therein to timely receive accurate values obtained by the sensor regarding the anesthetic agent and thereafter control the vaporization of anesthetic agent from the cassette 10.

What is claimed is:

1. A cassette for vaporization of anesthetic agent for delivery to a patient when the cassette is received by an anesthesia machine, the anesthesia machine having control mechanisms for controlling vaporization of the agent, the cassette comprising:

a housing having a reservoir for receiving, containing and emitting anesthetic agent;

a sensor embedded within the reservoir of the housing for obtaining a value of the agent contained in the reservoir, the sensor operatively connected to the reservoir to obtain an accurate value of the agent; and a communication link provided between the sensor and the control mechanisms of the anesthesia machine when the cassette is received by the anesthesia machine.

2. The cassette of claim 1, wherein the sensor is a pressure sensor that senses the pressure of fresh gas and anesthetic agent vapor in the reservoir.

3. The cassette of claim 1, wherein the sensor is a temperature sensor that senses the temperature of the anesthetic agent vapor in the reservoir.

4. The cassette of claim 3, wherein the temperature sensor is a thermistor.

5. The cassette of claim 1, further comprising an absorbent wick contained within the housing for absorbing anesthetic agent and allowing anesthetic agent to vaporize into gas for delivery to the patient.

6. The cassette of claim 5, wherein the sensor is in contact with the absorbent wick.

7. The cassette of claim 6, further comprising a bracket for securing the sensor against the absorbent wick.

8. The cassette of claim 7, wherein the bracket is formed of absorbent wick material.

9. A cassette for vaporization of anesthetic agent for delivery to a patient when the cassette is received by an anesthesia machine, the anesthesia machine having control mechanisms for controlling vaporization of the agent, the cassette comprising:
- a housing having a reservoir for receiving, containing, and emitting anesthetic agent;
- a sensor embedded in the reservoir of the housing for obtaining a value of the agent contained in the reservoir;
- a communication link provided between the sensor and control mechanisms of an anesthetic machine when the cassette is received by the anesthetic machine;
- an absorbent wick contained within the housing for absorbing anesthetic agent; and wherein the sensor contacts the absorbent wick at a location where anesthetic agent is vaporized.

10. An arrangement for a cassette for vaporization of anesthetic agent for delivery to a patient when the cassette is received by an anesthesia machine, the arrangement comprising:
- an anesthesia machine comprising control mechanisms for controlling vaporization of the anesthetic agent;
- a cassette removably received by the anesthesia machine, the cassette comprising a housing having an anesthetic agent reservoir for containing anesthetic agent;
- at least one sensor embedded in the reservoir of the housing and operatively connected to the reservoir, the sensor for obtaining a value of the agent contained in the reservoir; and
- a communication link provided between the sensor and the control mechanisms when the cassette is received by the anesthesia machine;
- wherein the control mechanisms are arranged to control vaporization of anesthetic agent based upon the value obtained by the sensor.

11. The arrangement of claim 10, wherein the sensor is a pressure sensor that senses the pressure of fresh gas and anesthetic agent vapor in the reservoir.

12. The arrangement of claim 10, wherein the sensor is a temperature sensor that senses the temperature of the anesthetic agent vapor in the reservoir.

13. The arrangement of claim 12, wherein the temperature sensor is a thermistor.

14. The arrangement of claim 10, wherein the cassette further comprises an absorbent wick for absorbing anesthetic agent and the sensor contacts the absorbent wick.

15. The arrangement of claim 14, wherein the sensor is coupled to the absorbent wick.

16. The arrangement of claim 10, wherein the communication link comprises an elongated circuit board.

17. The arrangement of claim 16, wherein the sensor is attached to the elongated circuit board and the elongated circuit board is operatively connected to the control mechanisms when the cassette is received by the anesthesia machine.

18. The arrangement of claim 17, wherein the elongated circuit board is operatively connected to the control mechanisms via a printed circuit board integrated with the cassette.

* * * * *